United States Patent
Chen

(10) Patent No.: US 7,064,213 B1
(45) Date of Patent: Jun. 20, 2006

(54) METHOD FOR PREPARING 2-(2-PYRIDYLMETHYLSULPHINYL)BENZIMIDAZOLES

(75) Inventor: Chih-Hung Chen, Hsinchu (TW)

(73) Assignees: Industrial Technology Research Institute, Hsinchu (TW); Syn-Tech Chem & Pharm Co., Ltd., Tainan Hsien (TW)

( * ) Notice: Subject to any disclaimer, the term of this patent is extended or adjusted under 35 U.S.C. 154(b) by 0 days.

(21) Appl. No.: 11/115,160

(22) Filed: Apr. 27, 2005

(30) Foreign Application Priority Data

Dec. 10, 2004 (TW) ............... 93138386 A

(51) Int. Cl.
*C07D 401/12* (2006.01)
(52) U.S. Cl. .................................. 546/272.7
(58) Field of Classification Search .............. 546/273.7
See application file for complete search history.

(56) References Cited

U.S. PATENT DOCUMENTS

| 5,374,730 | A * | 12/1994 | Slemon et al. | ........... 546/273.7 |
| 2004/0138466 | A1* | 7/2004 | Avrutov et al. | ........... 546/273.7 |

FOREIGN PATENT DOCUMENTS

ES 2063705 * 6/1993

OTHER PUBLICATIONS

Rouchard et al., "Catalysis of the oxidation, etc.," Bulletin de la Societe Chimque de France (1980), 9-10, Pr. 2, pp. 441-443.*
Bortolini et al., "Metal catalysts in oxidation etc.," CA 97: 55094 (1982).*

* cited by examiner

*Primary Examiner*—Patricia L. Morris
(74) *Attorney, Agent, or Firm*—Bacon & Thomas, PLLC

(57) ABSTRACT

The present invention provides a method for preparing an antiulcer agent, 2-(2-pyridylmethylsulphinyl)benzimidazoles, such as Omeprazole, Lansoprazole and Pantoprazole, which includes oxidizing an intermediate having a linkage of methylthio group ($-CH_2S-$) to methylsulfinyl ($-CH_2S(O)-$) in the presence of an oxidation catalyst of acetyl acetonate of molybdenium (II) [$(CH_3C(O)CH_2C(O)CH_2)_2Mo$].

16 Claims, No Drawings

METHOD FOR PREPARING 2-(2-PYRIDYLMETHYLSULPHINYL) BENZIMIDAZOLES

FIELD OF THE INVENTION

The present invention provides a method for preparing an antiulcer agent, 2-(2-pyridylmethylsulphinyl)benzimidazoles, such as Omeprazole, Lansoprazole and Pantoprazole, and particularly to a catalyst for the oxidation reaction in the preparation method.

BACKGROUND OF THE INVENTION

Many patents have disclosed a series of 2-(2-pyridylmethylsulphinyl)benzimidazoles as excellent agents for inhibiting the secretion of gastric acid, for example 5-methoxy-2-[(4-methoxy-3,5-dimethyl-2-pyridyl)methylsulfinyl]-1 H-benzimidazole (generic name: Omeprazole), 2-[[3-methy-4-(2,2,2-trifluoroethoxy)pyrid-2-yl]methylsulfinyl]-1 H-benzimidazole (generic name: Lansoprazole), and 5-Difluoromethoxy-2-[(3,4-dimethoxy-2-pyridyl-methylsulfinyl)-1 H-benzimidazole] (generic name: Pantoprazole). One common technical feature for the preparation of these benzimidazole compounds includes that individual precursors 1, 2, or 3 need to undergo similar oxidation reactions to form sulfinyl final products. According to European Patent EP0302720, a method for preparing Lansoprazole comprises oxidizing 2-[[3-methyl-4-(2,2,2-trifluoroethoxy)-2-pyridyl]methylthio]-1H-benzimidazole using $H_2O_2$ in the presence of a $V_2O_5$ catalyst. Other than the above-mentioned $V_2O_5/H_2O_2$ method, other oxidation methods for preparing Omeprazole, Lansoprazole, and Pantoprazole include m-chloroperbenzoic acid (MCPBA) (U.S. Pat. No. 4,628,098, U.S. Pat. No. 5,386,032), sodium perborate tetrahydrate ($NaBO_3 \cdot 4H_2O$)/$H_2O_2$ [WO99/02521(1999)], ammonium molybdate $((NH_4)_2MoO_4)/H_2O_2$ (ES Patent 2,036,948 (1993)).

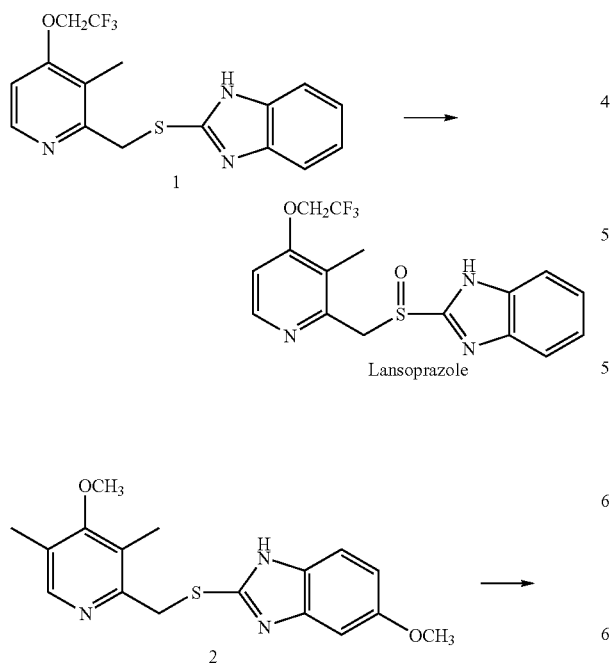

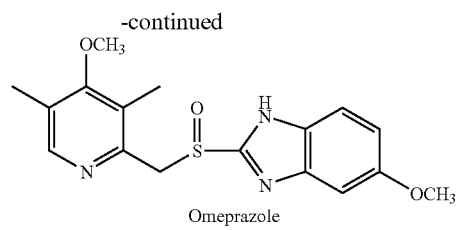

Omeprazole

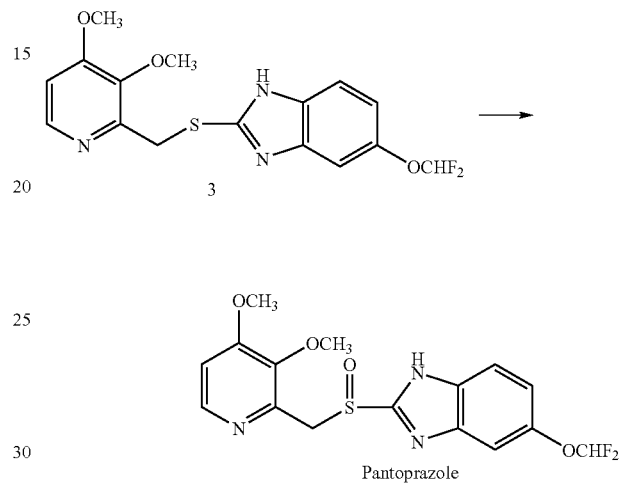

Pantoprazole

According to prior art, the inventor of the present invention used $V_2O_5$ as an oxidation catalyst and used $H_2O_2$ for the oxidation reaction of Lansoprazole and Omeprazole. Although the reaction ratio can reach above 90% and the oxidation by-products can be controlled to be within 1–2%, the reaction products are liable to become black and cannot be discolored. Therefore, the method is rather difficult in quality control. MCPBA is a conventional catalyst commonly used in the oxidation production of Omeprazole, Lansoprazole, and Pantoprazole, etc. However, when MCPBA is used as an oxidant, the reaction temperature is −20° C.~−60° C., and MCPBA is expensive. Under consideration of the low-temperature reaction condition and the production cost, such a method has substantial difficulties in mass production. The inventor of the present invention also conducted investigations in using $NaBO_3 \cdot 4H_2O/H_2O_2$ for the oxidation reaction of Lansoprazole, wherein, even though the reaction ratio can reach around 90%, excessive amount (5%–10%) of oxidation by-products having the following formula I and II are formed:

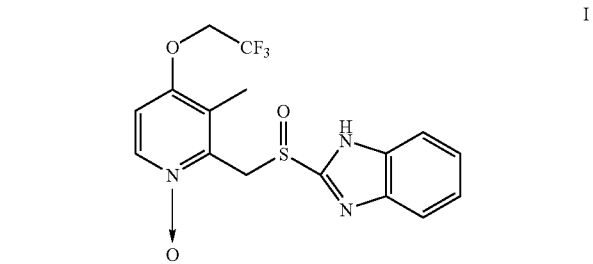

I

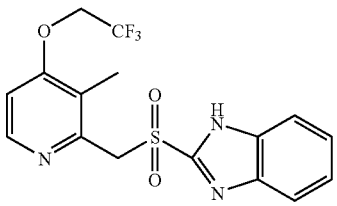

The physical properties of the by-products I and II are rather close to the physical properties of the desired product. Thus, the desired product, after crystallization purification of the reaction product mixture, are rather difficult to be separated from the by-products I and II. If further elaborate purifications are performed, the yield is liable to drop dramatically.

When $(NH_4)_2MoO_4/H_2O_2$ is used as an oxidant rather than $NaBO_3.4H_2O/H_2O_2$, more oxidation by-products I and II (8~20%) are produced, and the total yield is about 75%. Thus, such a process is not industrially feasible.

It can be understood from the above that the industry is still looking for a method for commercially mass production of 2-(2-pyridylmethylsulphinyl)benzimidazoles, such as Omeprazole, Lansoprazole and Pantoprazole, with mild reaction conditions, capable of effectively inhibiting excessive formation of the oxidation by-products I and II, and simple in purification of the desired products.

SUMMARY OF THE INVENTION

The present invention discloses a method for preparing 2-(2-pyridylmethylsulphinyl)benzimidazole having the following formula [A], which comprises undergoing an oxidation reaction of an intermediate having the following formula [B] in a solvent and in the presence of a catalyst and an oxidant to form the compound [A]:

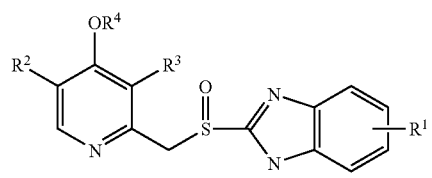

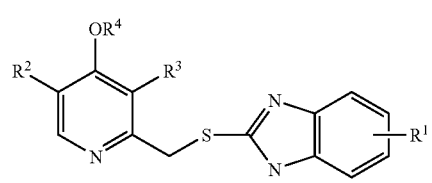

wherein $R^1$ in [A] and [B] is hydrogen, halogen, C1–C6 alkyl, C1–C6 alkoxy, halogenated C1–C6 alkyl, or halogenated C1–C6 alkoxy; $R^2$ and $R^3$ independently are hydrogen, halogen, C1–C6 alkyl, C1–C6 alkoxy, halogenated C1–C6 alkyl, or halogenated C1–C6 alkoxy; and $R^4$ is hydrogen, halogen, C1–C6 alkyl, or halogenated C1–C6 alkyl;

characterized in that said catalyst is acetyl acetonate of molybdenium (II), titanium, cobalt, or copper, and preferably acetonate of molybdenium (II).

Preferably, said oxidant is $H_2O_2$, tert-butylhydroperoxide, or Cumene hydroperoxide.

Preferably, in said solvent is C1–C6 alcohol, chlorinated C1–C4 alkane, or ethyl acetate. More preferably, said solvent is methanol, ethanol, iso-propanol, n-butanol, or iso-butanol. More preferably, said solvent is dichloromethane, dichloroethane, or ethyl acetate.

Preferably, said oxidation reaction is carried out in a homogeneous phase solvent or a two-phase solvent.

Preferably, said oxidation reaction is carried out in the two-phase solvent, and an interphase transfer catalyst is added to the two-phase solvent, so that the oxidation reaction is carried out under the presence of said interphase transfer catalyst, wherein said interphase transfer catalyst is selected from the group consisting of quaternary ammonium salt, quaternary phosphate salt, polyether, and crown ether.

Preferably, said oxidation reaction is carried out in a temperature of −15~30° C.

Preferably, a weight ratio of said solvent to said intermediate [B] is 2:1 to 20:1 in the oxidation reaction.

Preferably, a mole ratio of said oxidant to said intermediate [B] is 1:1 to 5:1 in the oxidation reaction.

Preferably, a weight ratio of said catalyst to said intermediate [B] is 3% to 20% in the oxidation reaction.

Preferably, said compound [A] is Lansoprazole.
Preferably, said compound [A] is Omeprazole.
Preferably, said compound [A] is Pantoprazole.

The present invention adopts an organic composite catalyst, e.g. molybdenyl acetyl acetone (also named as acetylacetonate of molybdenium) (hereinafter abbreviated as $Mo(acac)_2$), together with an oxidant, for the oxidation reaction of the precursors of benzimidazole compounds, such as Omeprazole, Lansoprazole, and Pantoprazole. According to the present invention, the reaction conditions are mild without severe temperature conditions. Furthermore, a Mo-series catalyst is less toxic than a vanadium catalyst. Most importantly, the reaction produces a rather small amount of the by-products I and II (1–2%). Accordingly, a preparation method according to the present invention is far superior in comparison to the conventional preparation methods. Thus, the method for preparing a thio-containing antiulcer agent, such as Omeprazole, Lansoprazole and Pantoprazole, according to the present invention is improved over the conventional methods and applicable for mass production.

DETAILED DESCRIPTION OF THE INVENTION

A method according to the present invention comprises separately preparing precursor intermediates 1, 2, 3 of Omeprazole, Lansoprazole, and Pantoprazole; preparing a suitable solvent such as methanol, ethanol, and propanol, or a two-phase solvent of water and ethyl acetate, dichloromethane, dichloroethane, or tetrahydrofuran, wherein an interphase transfer catalyst (e.g. quaternary ammonium salt, polyether, quaternary phosphate salt, or crown ether (preferably polyether, or crown ether)) is added to the two-phase solvent; adding the intermediate and a catalyst $Mo(acac)_2$ into the solvent; and finally adding batchwise or in one lot an oxidant into the resulting mixture to undergo an oxidation reaction at 0–30° C. A suitable oxidant is selected from the group consisting of $H_2O_2$, sodium percarbonate, tert-butylhydroperoxide (abbreviated as TBHP), cumene hydroperoxide, and Fremyl's salt, wherein $H_2O_2$ and TBHP are preferable.

EXAMPLE 1

2.68 g of 2-chloromethyl-3-methyl-4-(2,2,2-trifluoroethoxy)pyridine.HCl, 1.376 g of 2-mercaptobenzimidazole, and 0.134 g of benzyl triethyl ammonium chloride as an interphase transfer catalyst were mixed in 24 ml of dichloromethane. 0.9534 g of NaOH (40%)/12 ml water mixture solution was dripped into the above mixture while stirring. The temperature of the resulting solution was raised to 40° C. for about 2 hours. Then, dichloromethane was removed from the mixture under a reduced pressure. The solid obtained was stirred with 50 ml of water, and filtered to obtain 3.28 g of solid Lansoprazole precursor: 2-[[3-methyl-4-(2,2,2-trifluoroethoxy)-2-pyridyl]methylthio]-1H-benzimidazole. At room temperature, 3.28 g of the above precursor, 0.1625 g of polyethylene glycol-400 as an interphase transfer catalyst, and 0.3936 g of Mo(acac)$_2$ as an oxidation catalyst were mixed in 45 ml of isopropanol (abbreviated as IPA). To the resulting mixture 3.06 g of 35% $H_2O_2$ aqueous solution was added in 5–10 minutes. The reaction was carried out for about one hour, and then 60 ml of water was added, and the reaction was continued for another one hour while stirring. Finally, the precipitate formed was filtered, water washed, and dried to obtain Lansoprazole with a yield of about 88% (HPLC purity>98%).

EXAMPLE 2

At room temperature, 1.307 g of 2-[[3-methyl-4-(2,2,2-trifluoroethoxy)-2-pyridyl]methylthio]-1H-benzimidazole, 0.059 g of tetrabutyl ammonium bromide as an interphase transfer catalyst, and 0.157 g of Mo(acac)$_2$ oxidation catalyst were mixed in 15 ml of IPA. Next, 1.36 g of TBHP (70% aqueous solution) was added into the mixture in about 5–10 minutes. The reaction was carried out for about 30 hours, and then 60 ml of water was added, and the reaction was continued for another one hour while stirring. Finally, the precipitate formed was filtered, water washed, and dried to obtain Lansoprazole with a yield of about 37% (HPLC purity>96%).

EXAMPLE 3

3 g of Omeprazole precursor: 2-[(3,5-dimethyl-4-methoxy-2-pyridyl)methylthio]-5-methoxy-1H-benzimidazole, 0.09 g of Mo(acac)$_2$ oxidation catalyst were dissolved in 20 ml of methanol by stirring. The temperature of the resulting solution was reduced to 0–5° C., followed by adding 1.17 g of 35% $H_2O_2$ aqueous solution. The reaction was carried out for about two hours, and then 60 ml of water was added, and the reaction was continued for another one hour while stirring. Finally, the precipitate formed was filtered, water washed, and dried to obtain Omeprazole with a yield of about 91–92% (HPLC purity>98%).

EXAMPLE 4

3.17 g of Pantoprazole precursor: 5-difluoromethoxy-2-[(3,4-dimethoxy-2-pyridyl)methylthio]-1H-benzimidazole, 0.095 g of Mo(acac)$_2$ oxidation catalyst were dissolved in 20 ml of methanol. The temperature of the solution was reduced to 0–5° C. To the solution 1.17 g of 35% $H_2O_2$ aqueous solution was added and the reaction was carried out for about two hours, and then 60 ml of water was added, and the reaction was continued for another one hour while stirring. Finally, the precipitate formed was filtered, water washed, and dried to obtain Pantoprazole with a yield of about 60% (HPLC purity>98%).

The invention claimed is:
1. A method for preparing 2-(2-pyridylmethylsulphinyl) benzimidazole having the following formula [A], which comprises undergoing an oxidation reaction of an intermediate having the following formula [B] in a solvent and in the presence of a catalyst and an oxidant to form the compound [A]:

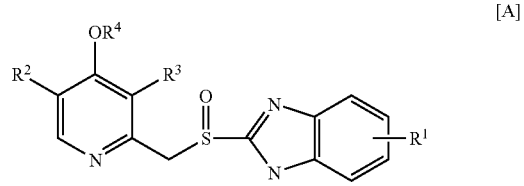

[A]

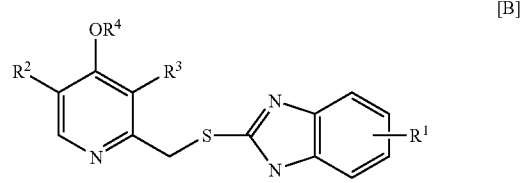

[B]

wherein $R^1$ in [A] and [B] is hydrogen, halogen, C1–C6 alkyl, C1–C6 alkoxy, halogenated C1–C6 alkyl, or halogenated C1–C6 alkoxy; $R^2$ and $R^3$ independently are hydrogen, halogen, C1–C6 alkyl, C1–C6 alkoxy, halogenated C1–C6 alkyl, or halogenated C1–C6 alkoxy; and $R^4$ is hydrogen, C1–C6 alkyl, or halogenated C1–C6 alkyl; characterized in that said catalyst is acetyl acetonate of molybdenium (II).

2. The method as claimed in claim 1, wherein said oxidant is $H_2O_2$, tert-butylhydroperoxide, or Cumene hydroperoxide.

3. The method as claimed in claim 1, wherein said solvent is C1–C6 alcohol, chlorinated C1–C4 alkane, or ethyl acetate.

4. The method as claimed in claim 3, wherein said solvent is methanol, ethanol, iso-propanol, n-butanol, or iso-butanol.

5. The method as claimed in claim 3, wherein said solvent is dichloromethane, dichloroethane, or ethyl acetate.

6. The method as claimed in claim 1, wherein said oxidation reaction is carried out in a homogeneous phase solvent or a two-phase solvent.

7. The method as claimed in claim 6, wherein said oxidation reaction is carried out in the two-phase solvent, and an interphase transfer catalyst is added to the two-phase solvent, so that the oxidation reaction is carried out under the presence of said interphase transfer catalyst, wherein said interphase transfer catalyst is selected from the group consisting of quaternary ammonium salt, quaternary phosphate salt, polyether, and crown ether.

8. The method as claimed in claim 1, wherein said oxidation reaction is carried out in a temperature of −15~30° C.

9. The method as claimed in claim 1, wherein a weight ratio of said solvent to said intermediate [B] is 2:1 to 20:1.

10. The method as claimed in claim 1, wherein a mole ratio of said oxidant to said intermediate [B] is 1:1 to 5:1.

11. The method as claimed in claim 1, wherein a weight ratio of said catalyst to said intermediate [B] is 3% to 20%.

12. The method as claimed in claim 1, wherein said compound [A] is 2-[[3-methy-4-(2,2,2-trifluoroethoxy)pyrid-2-yl]methylsulfinyl]-1H-benzimidazole.

13. The method as claimed in claim 1, wherein said compound [A] is 5-methoxy-2-[(4-methoxy-3,5-dimethyl-2-pyridyl) methylsulfinyl]-1H— benzimidazole.

14. The method as claimed in claim 1, wherein said compound [A] is 5-Difluoromethoxy-2-[(3,4-dimethoxy-2-pyridyl-methylsulfinyl)-1H— benzimidazole].

15. The method as claimed in claim 7, wherein said interphase transfer catalyst is polyether.

16. The method as claimed in claim 15, wherein said, polyether is polyethylne glycol.

* * * * *